United States Patent [19]
Schmidt

[11] Patent Number: 5,683,368
[45] Date of Patent: Nov. 4, 1997

[54] CONTROLLED MOTION LOCK FOR SAFETY CATHETER

[75] Inventor: Philip Schmidt, Bistol, Conn.

[73] Assignee: Johnson & Johnson Medical, Inc., Arlington, Tex.

[21] Appl. No.: 716,575

[22] Filed: Sep. 19, 1996

[51] Int. Cl.⁶ .................................................. A61M 5/178
[52] U.S. Cl. ................................................ 604/164; 604/263
[58] Field of Search ................................. 604/158, 162, 604/164, 187, 263, 198, 171

[56] References Cited

U.S. PATENT DOCUMENTS

| | | |
|---|---|---|
| 4,762,516 | 8/1988 | Luther et al. . |
| 4,813,940 | 3/1989 | Parry .................................. 604/263 X |
| 4,826,490 | 5/1989 | Byrne et al. . |
| 4,944,041 | 7/1990 | Dombrowski et al. . |
| 4,944,725 | 7/1990 | McDonald . |
| 5,104,384 | 4/1992 | Parry .................................. 604/263 X |
| 5,215,528 | 6/1993 | Purdy et al. . |
| 5,295,974 | 3/1994 | O'Laughlin ....................... 604/171 X |

*Primary Examiner*—John D. Yasko
*Attorney, Agent, or Firm*—Joseph F. Shirtz

[57] ABSTRACT

An intravenous catheter insertion device which incorporates a controlled motion lock including telescopingly arranged slide members for a safety catheter constituting a needle tip protector mechanism which provides fail-safe protection for clinical personnel against the possibility of accidental punctures by a used IV cannula needle through catheter needle tip protecting structure which provides an audible signal that the protecting structure is fully deployed.

22 Claims, 2 Drawing Sheets ered fluids.

CONTROLLED MOTION LOCK FOR SAFETY CATHETER

BACKGROUND OF THE INVENTION

1. Field of the Invention

The present invention relates, in general, to intravenous catheter insertion devices, and especially pertains to a controlled motion lock for a safety catheter constituting a needle tip protector mechanism which provides fail-safe protection for clinical personnel against the possibility of accidental punctures by a used IV cannular needle through automatic catheter needle tip protecting structure which becomes operative upon withdrawal of the cannular needle from a venipuncture in the body of a patient.

In particular, pursuant to specific aspects of the invention, there is provided a catheter insertion device incorporating a sequentially operating multi-part locking structure in the nature of telescopable slides which are capable of being utilized in a considerable variety and types of catheter insertion devices. In essence, an important consideration which must be given to the aspect that there is present a safeguard for a catheter through essentially a "fail-safe" arrangement, whereby the used cannula or just the tip thereof is fully retracted into its protective structure, such as a needle tip protector or housing prior to disengagement thereof from a catheter hub. Concerning the foregoing, it has been noted that, upon occasion, needle stick by users of the device may be encountered in that the needle tip of the used cannula may still protrude to some extent, and resultingly pose a danger or hazard to clinical personnel or physicians using the catheter insertion device upon withdrawal thereof from a patient or, depending on the type of its design, during separation of the cannula assembly from the catheter and its attached catheter hub. In numerous constructions and designs of catheter insertion devices, for example, such as the currently employed so-called Luer lock versions or sideport catheters, various techniques and structures are employed for separating retracted used cannulae and their associated housings and needle protective structures from the respective catheter and catheter hub portion, the former of which is still inserted in the venipuncture formed in the body of a patient and which is adapted to be connected to various other sources of parenteral fluids, blood, medications and the like during intravenous fluid supplying procedures, as is well known in the medical technology.

An important aspect of the invention resides in being able to ensure that the structure of the controlled motion lock and the sequentially telescopable slide components of the needle tip protector for the used cannula or hollow needle which is being retracted will impart a clear indication as to the efficacy of the full retraction of the cannula, thereby ensuring not only a visual but also a single clearly audible assurance of such a protective procedure or final locking action having been implemented during the catheter and cannula separation process, and prior to the effecting of the release of the housing or structure which protectively contains the used cannula from a catheter hub.

Pursuant to a specific aspect of the invention, which may be applicable to various types of catheter insertion devices or safety catheters as described hereinbelow, there is provided a controlled motion lock structure comprising interlocking telescopable slide members whereby in a plurality of telescoping steps, the cannula, comprising the hollow needle, may be retracted into the needle tip protecting structure or guard housing in a step-by-step relationship as the slide members are telescopingly extended relative to each other so as to ultimately provide a locking arrangement generating a single clearly audible sound or "click", and concurrently therewith visual indication. Resultingly, this is informative to clinical personnel operating the catheter insertion device that the cannula has, in fact, been fully retracted into the needle tip protector or guard housing and protectively locked in place, and consequently will no longer pose any physical danger or hazard to the user or clinical personnel, thereby enabling the completion of safe separation of the needle or cannula guard housing or protective structure from the catheter hub.

The utilization of clinical apparatus in which pointed hollow steel needles or cannulae, frequently referred to as styli, are employed in order to puncture the skin of a patient, and especially safety catheters utilizing such needles to effectuate venipunctures, is well known in the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle, generally of surgical-quality steel, having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally generally constituted of surgical-quality steel, and while inserted into the vein of a patient, necessitated the needle to be maintained for reasons of safety in a fixed position at the general site of the venipuncture throughout the duration of fluid administration or transfusion, whereby such a procedure could conceivably consume a considerable length of time, posing the danger of the needle shifting and injuring the patient. In addition to the foregoing, at times it has been necessary to periodically draw blood samples and/or successively or intermittently administer intravenous fluids to a patient, thus requiring the patient to be subjected to a series or plurality of venipunctures, each administered at a specific time and at different sites on the body, resulting in a relatively traumatic experience to the patient in view of the implementation of such repeated and somewhat painful and unpleasant venipunctures.

In order to ameliorate or possibly even eliminate the foregoing problems, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopably and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom.

2. Discussion of the Prior Art

Although extendable or telescoping elements for protecting used cannulas of safety catheter insertion devices are currently known in the art, none of these discloses the use of interlocking sequenced telescoping slide members for the "fail-safe" retraction and protection of the cannulas, which will provide for a controlled motion lock incorporating a single and resultingly clearly distinct visual and audio indication of the locking efficacy thereof.

Thus, U.S. Pat. No. 4,950,252 to Luther et al. discloses a cannula guard and housing structure which are mutually relatively axially extendable for receiving therein a used cannula in a protective environment, but which does not provide for an audible signal that locking action has taken place.

McDonald U.S. Pat. No. 4,944,725 addresses the problem in disclosing an intravenous catheter which incorporates a structure for protecting a clinician or physician from accidental puncture which may result in the transfer of dangerous infections from the patient. The catheter is introduced into the patient's body with the aid of a needle of hollow or cannula construction which is thereafter withdrawn from the patient's body into a protective housing in the absence of exposing the needle during any intermediate stage of the withdrawing process. The housing is then latched in place subsequent to needle withdrawal, and for unlocking a catheter hub in place subsequent to that time, and effecting withdrawal and locking in one continuous motion.

Another publication which is applicable in providing for the protection of the point of a cannula or needle subsequent to or upon removal thereof from the body of a patient is disclosed in Dombrowski et al. U.S. Pat. No. 4,790,828, wherein a nose portion or cap is tethered to a housing by means of a collapsible tethering structure encompassing the needle such that the needle will be retracted into a sheath-like expanding arrangement which will securely prevent potential injury to clinical personnel which can be caused by being jabbed by an exposed used point of the needle.

More recently, there has been developed a catheter arrangement with interlocking sequence guarding members for the protection of a cannula, whereby a plurality of telescopingly arranged elongate slide elements or guarding members include a plurality of axially spaced interengagable detents and locking projections so as to, in sequential steps provide for an initial locking engagement and thereafter, upon further extension of a cannula guarding structure complete a final interengagement of the telescopable guarding members which will protectively house the needle tip structure of the cannula. During the extension of the guarding members, there are provided two subsequent audible signals, the first indicating that the initial locking step has been implemented between the guarding members, and the second audible signal being indicative that the final locking step or sequence has been accomplished, thereby rendering the catheter safe to handle with the needle being a fully retracted position. This successive audible signal generating sequence, however, is so closely spaced in time that unless the user counts the two closely following signals to be sure the device is fully extended and locked, this may cause confusion since it conceivably may be assumed upon hearing the first audible signal that the needle is fully retracted, which in actuality is not the case. A device of that type is described in commonly assigned copending U.S. patent application No. 08/483950 filed Jun. 7, 1995, which although generally satisfactory in use is of a relatively complex nature in operation and construction and, at times, renders it difficult for a user to clearly ascertain the two successively generated audio signals.

SUMMARY OF THE INVENTION

Accordingly, in order to afford an improved structure in the provision of a protective arrangement for a used cannula, and especially a controlled motion lock for a safety catheter which will ensure a practically "fail-safe" operation, the present invention contemplates the provision of a multi-part locking device including telescopably movable slide members. In that instance, a plurality of slide members, generally designated as a primary slide and at least one or more secondary slides, are adapted to be positioned so as to be extendible from a housing having the cannula fastened to a chamber located in the latter so as to project axially therefrom, and with the cannula being essentially in a parallel-axial relationship with the slide members. The extending leading end of the primary telescopable slide amounts a needle protector secured thereto, with a catheter extending over the needle or cannula being seated onto the tip protector. Upon the needle having been inserted into the body of the patient, and the catheter lodged in the vein of the patient, in order to provide for protection and retraction of the cannula and needle, the primary and secondary slides are concurrently moved forward until one of the secondary slides has the trailing end thereof engaging a locking post which consists of a part of the housing for a cannula-mounting chamber, such as a blood chamber, or subsequent secondary slide, so as to inhibit any further forward movement of the secondary slides. Thereafter, the primary slide is advanced further forwardly, in conjunction with the cannula or needle tip protector mounted thereon so as to expose a spring tab on the secondary slides which will deflect downwardly and engage the locking post to thereby cause the secondary slides to be fully locked into a fixed position relative to the housing. The primary slide with the needle tip protector mounted at the front end thereof is then advanced still further forwardly to a position in which a further spring tab cut into the secondary slides proximate the front end thereof deflects to engage into a window or cutout formed in the rearward end portion of the primary slide, this resultingly producing a clearly ascertainable snapping sound providing an audio signal indicative that the primary slide is fully extended from the housing whereby the needle tip protector fully encompasses the needle tip and cannula. A further opening formed in the leading end of the primary slide is adapted to provide visual indication that the primary and secondary slide members are in their fully extended and mutually locked position in which the needle tip protector fully encompasses the cannula or its tip and affords protection to medical or clinical personnel against needle stick or any other hazards which may be encountered in the handling of the used safety catheter.

Accordingly, it is an object of the present invention to provide a catheter insertion device or a safety catheter incorporating a controlled motion lock with a multi-step locking sequence for the protective housing of a used cannula.

Another object of the present invention is to provide a telescopable slide arrangement forming a multi-part controlled motion lock for a safety catheter which, upon withdrawal of a cannula from a patient will provide for the sequential extension of slide members relative to a housing structure mounting the cannula so as to ensure the complete and safe confinement of the cannula in a protective environment.

Still another object of the present invention resides in the provision of a safety catheter incorporating a multi-step locking action through a controlled motion lock device in which a plurality of mutually coaxially displaceable slide members are adapted to be extended so as to position a needle tip protector mounted on one of the slide members over a cannula needle tip upon removal of the latter from the body of a patient, and which motion lock device, upon the extended position of the slide members being reached, will generate a single audio signal which is indicative that the controlled motion lock is in its fully operative position, imparting information as to the efficacy of the locking action apprising a user of the positioning of the cannula in its protective environment.

BRIEF DESCRIPTION OF THE DRAWINGS

Reference may now be had to the following detailed description of an exemplary embodiment of the invention, taken in conjunction with the accompanying drawings; in which.

DETAILED DESCRIPTION OF A PREFERRED EMBODIMENT

Figure 4:
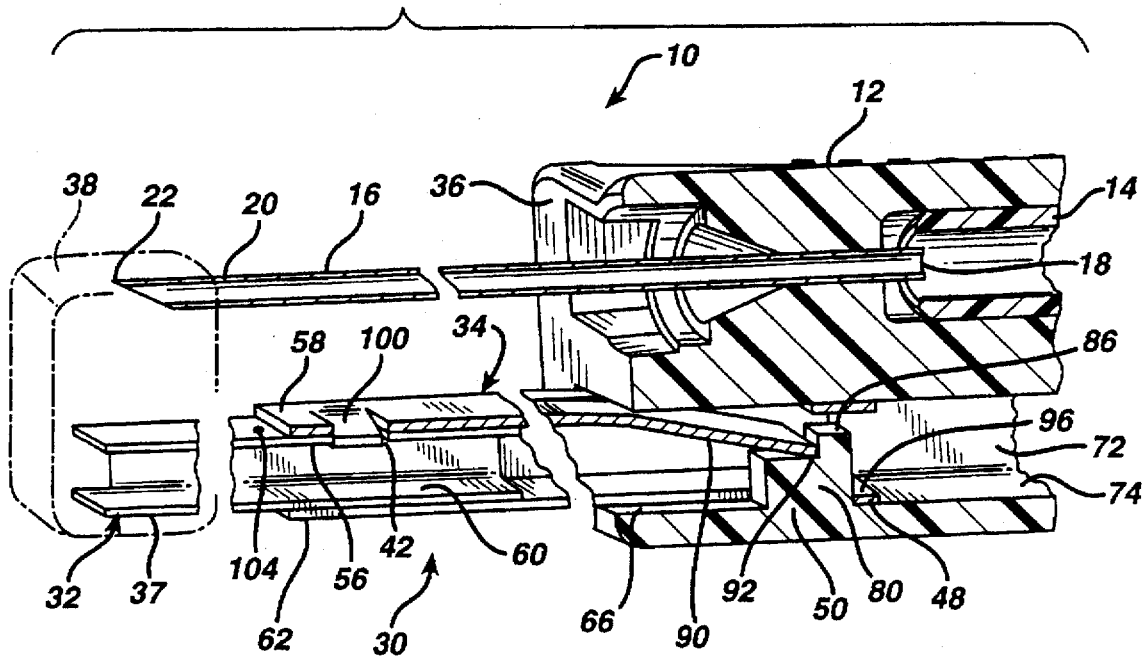
FIG. 4 illustrates the forward end of the arrangement of FIG. 3, showing the final locking engagement of the slide members in the fully extended cannula-protective operative position of the controlled motion lock.

Referring now in detail to the drawings, there is disclosed the forward end portion of a safety catheter 10, shown in longitudinal cross-section, including a housing 12 incorporating a blood chamber 14 mounting a cannula 16 at a trailing end 18 thereof. The leading end 20 of the cannula 16, which may be a steel stylet, as shown in FIG. 4 of the drawings, terminates in a sharp needle tip 22 which is adapted for insertion into the body of a patient so as to form a venipuncture to enable the introduction of parenteral fluids, blood or the like, or for the withdrawal of blood specimen into chamber 14. Extending over the cannula 16 may be a catheter (not shown) of a suitable material, such as a soft silastic or plastic material which is concurrently introduced into the body of the patient and remains therein at the site of the venipuncture upon withdrawal of the cannula 16, as mentioned hereinabove.

In order to provide for a needle guarding or protecting environment, there is provided a telescopable controlled motion lock 30 in the manner of mutually coaxially telescopingly displaceable elongate slide members 32, 34 which are adapted to be extended forwardly from the forward end 36 of housing 12 in parallel spaced relationship with the axial run of the cannula 16. The slide members 32, 34 which comprise a primary slide 32 and a secondary slide 34, each being of generally box-like transverse cross-section, and in which the at least one secondary slide 34 may be constituted of a metallic sheet metal structure possessing resiliently flexible properties as described hereinbelow.

Figure 1:
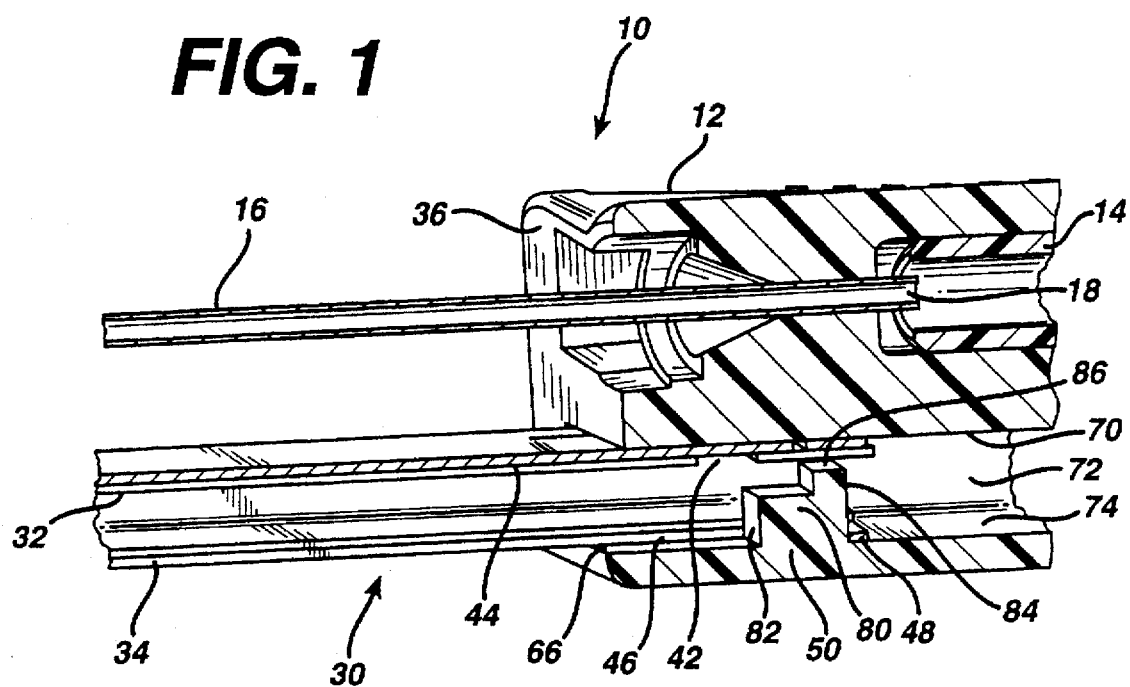
FIG. 1 illustrates a generally diagrammatic perspective longitudinal sectional view of the inventive controlled motion lock for a safety catheter, shown in the fully seated position of the slide members.

Mounted at the leading end 37 of the primary slide 32 as shown in schematic block representation in FIG. 4 of the drawing, is a protector housing or guard 38 for encompassing the needle tip 22 of cannula 16. Towards the rearward end 40 of the primary slide 32, which as shown in FIG. 1 is located within the housing 12, the slide 32 includes a cutout portion, forming a recess or window 42 which is in contact with the adjoining surface 44 of the secondary slide 34 so as to be in close slidable engagement therewith.

The secondary slide 34 which essentially extends closely about the primary slide 32 along the extent thereof, includes at its rearward end 46 a lateral extension or protuberance 48 which, upon the slide 34 being drawn forwardly towards the forward end of the housing 12 from which the cannula 16 protrudes, is adapted to engage a locking post 50 formed on the housing.

As indicated hereinabove, and as illustrated in the longitudinal sectional view drawings, each of the slides 32, 34 is essentially of a box-like cross-section having each, respectively, upstanding outside planar walls 52, 54, a top 56, 58; and slotted bottom 60, 62. As mentioned, the secondary slide 34 is in close sliding contact with the primary slide 32 and extends encompassingly externally thereof, having the outside walls, top and bottom 54, 58 and 62 with inward surfaces thereof in close sliding contact with the outer surfaces 52, 56 and 60 of the primary slide 32.

The housing 12, which is shown in longitudinal sectional view, includes a recess 66 of generally rectangular shape extending along the path of the axial movement of the slides 32, 34 within the housing, whereby the outer surfaces 54, 58, 62 of the secondary slide 34 are in close contact along the walls 70, 72, 74 of the recess 66 in the housing 12, whereby the outer surface of the top 58 of the secondary slide 34 glides along surface 70 in housing recess 66, the outer surface of the bottom 62 of the secondary slide 34 is in contact with the surface 74 of the recess 66, whereas the outer surface of the wall 54 of the secondary slide 34 glides along the wall 72 of the recess 66.

Integrally formed to extend upwardly from the surface 74 of the housing recess 66 is a stepped member 80 which constitutes a locking post adapted to restrict the forward movement of the secondary slide 34 and lock the latter in a predetermined axially displaced position, as described hereinbelow. In this connection, the locking post 80 includes a first upstanding stepped portion 82 which towards the rear thereof in the recess 66 of the housing 12 includes a further more upwardly protruding stepped surface portion 84, each portion 82, 84 being of generally rectangular configuration, with the upper surface 86 of surface portion 84 extending into close proximity with the inner surface of top 56 of the primary slide 32.

Figure 2:
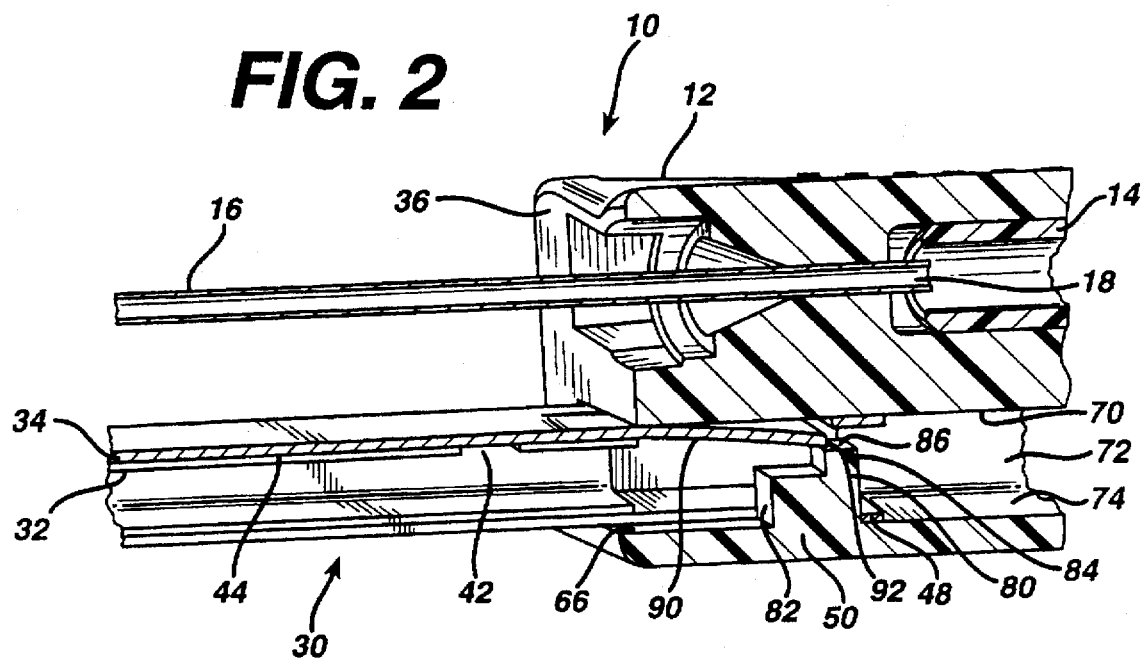
FIG. 2 illustrates the controlled motion lock with the slide members thereof in a partially forwardly extended position.
Figure 3:
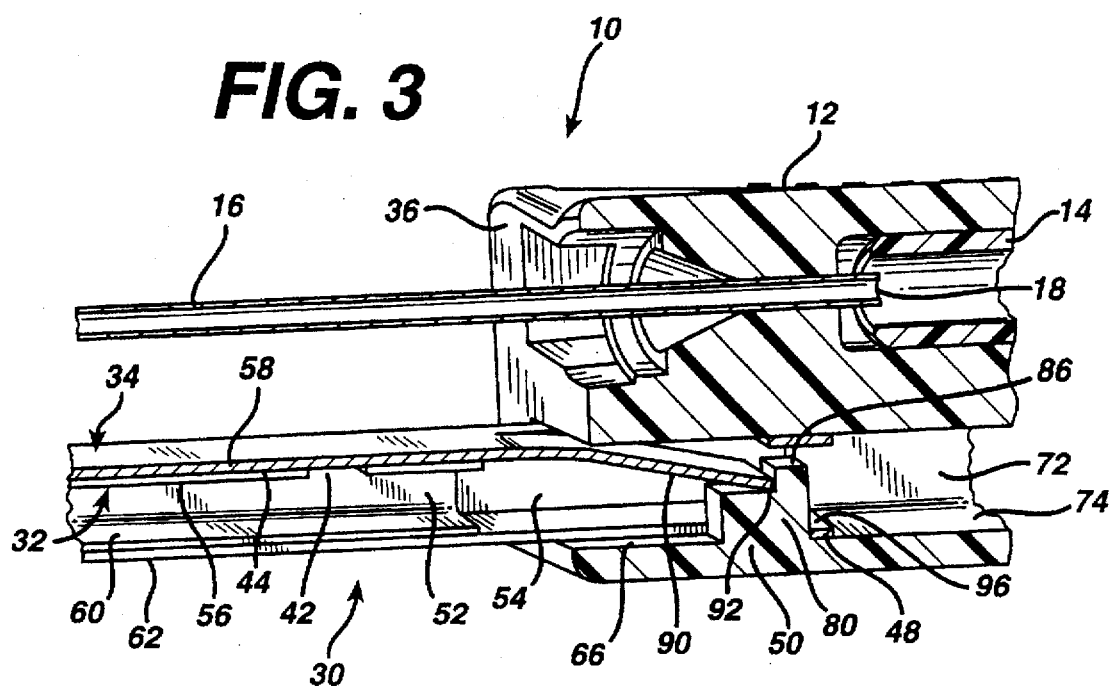
FIG. 3 illustrates a primary slide member of the slide members in a fully extended position in which a secondary slide member of the controlled motion lock is completely engaged with a locking post on the cannula mounting housing.

The forward movement of the secondary slide 34 relative to the housing 12 is limited in that the bottom 62 at its rearward end includes a laterally protruding element 96 which, in the forward most position of the secondary slide 34 engages the rear surface of the locking post 80, as shown in FIGS. 1 through 3 of the drawings, thereby inhibiting any further forward displacement of the secondary slide 34 relative to the housing 12.

Upon the secondary slide 34 having been moved forward in housing recess 60 to the position shown in FIGS. 1 through 3, and the primary slide 34 being further forwardly displaced, as shown in FIG. 3 of the drawings, the tab portion 90 in the top 58 of the secondary slide 34 deflects downwardly, contacting the upper surface of the lower stepped portion 82 of the locking post 80 with the trailing end of primary slide 32 having been further advanced within the secondary slide 34 so as to clear the locking post 80. The rear or trailing end of the primary slide 32 having passed the locking post 80, the tab portion 90 of the secondary slide 34 is thus downwardly deflected to its full extent, as shown in FIG. 3 of the drawings, whereby the rear tab edge 92 of the secondary slide 34 rests on the upper surface of the lower stepped portion 82 of the locking post 80. Consequently, the rear edge 92 of the downwardly deflected tab portion 90 which now contacts the front surface of the higher stepped portion 84 of the locking post 80, and in conjunction with the laterally protruding element 96 in the bottom 62 at the rear end of the secondary slide 34 causes the secondary slide to be securely engaged in an axially locked position with the locking post 80, as shown in FIG. 3 of the drawings. This indicates that the tab 90 of the secondary slide 34 is in locked position on locking post 80, and the primary slide 32 has been moved fully away from the locked tab portion 90, and is being advanced further forwardly out of housing 12.

The primary slide 32, when continued in its forward motion, has the window or recess 42 therein adapted to be engaged by a further spring-like deflectable tab portion 100 formed in the flange 58 of the secondary slide 32 towards the front end of the latter, which, upon the recess or window 42 in the primary slide 32 coming into alignment therewith snaps into the window 42, thereby engaging the primary slide 32 in its foremost extended position relative to the secondary slide 34, and with the tip protector or guard housing 38 mounted on the leading end 36 thereof completely and protectively encompassing the sharp-tipped point 22 of the cannula 16.

The foregoing two-part extending motion of the slide members 32, 34 generates a single audible snapping or clicking sound when the second spring tab portion 100 which is formed towards the front end of the secondary slide 34 snaps into the recess or locking window 42 located towards the back end portion of the primary slide 32. This snap provides the one and only audible signal that the controlled motion lock has been activated and that the needle tip protector 38 is safely and securely positioned over the tip 22 of the cannula 16, and is locked in place to render it unable to be further advanced or retracted.

In order to provide for visual indication of the foregoing, a safety indicator aperture 104 may be stamped into the primary slide 32 just beyond the front or leading edge of the secondary slide 34 and in the extended locked position of the slide members provides visual proof that the device is safely locked.

While there has been shown and described what is considered to be a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A controlled motion lock arrangement for protecting a cannula of a catheter insertion device, comprising:
    (a) a housing for receiving a first end of a cannula, said cannula extending from an end of said housing coextensively with a longitudinal axis of said housing and having a sharp-tipped point at a second end adapted to introduce a catheter into a patient;
    (b) multi-part slide means axially slidable within a longitudinal recess formed in said housing so as to be extendable from the end of said housing receiving said cannula in parallel spaced relationship with said cannula, said slide means comprising:
        (i) a first slide member in slidable contact with wall surfaces of said housing recess, means on said first slide member engageable with a locking post structure formed in said housing recess for limiting the extent of outward movement of said first slide member from said housing;
        (ii) at least one second slide member arranged within said first slide member so as to be axially displaceable with respect to said first slide member; cannula tip guarding means being mounted on a leading end of said second slide member; means locking said first slide to said locking post upon said at least one second slide member being extended; and means locking said at least one second slide member to said first slide member in the outermost extended positions of said slide members while generating an audible signal indicative thereof and said guarding means protectively extends about the cannula tip.

2. An arrangement as claimed in claim 1, wherein said locking post comprises a stepped structure, said first slide member having a lateral protuberance at the trailing end engageable with said locking post to limit axial movement of said first slide member from said housing.

3. An arrangement as claimed in claim 2, wherein a resiliently deflectable tab is formed in said first slide member proximate the trailing end thereof, said at least one second slide member when fully retracted within said first slide member inhibiting deflection of said tab and, upon being extended outwardly of said first slide member, releasing said tab such that said tab deflects into engagement with a forward surface on said locking post and in cooperation with said lateral protuberance locks said first slide member into locked engagement with said locking post.

4. An arrangement as claimed in claim 1, wherein a cutout is provided in said at least one second slide member proximate the rearward end thereof; a resiliently deflectable tab being formed in said first slide member proximate the forward end thereof, whereby upon predetermined extension of said at least one second slide member relative to said first slide member, said resiliently deflectable tab engages into said cutout so as to lock said slide members into relative extended positions while concurrently generating an audible sound during engagement of said tab in said cutout indicative of the locking together of said slide members.

5. An arrangement as claimed in claim 1, wherein said slide members are each of generally box-shaped configuration in cross-section, said means for locking said first slide member to said locking post and said means for locking said at least one second slide member to said first slide member being formed in at least one wall surface of the respective slide member.

6. An arrangement as claimed in claim 5, wherein said slide members are each constituted of a metallic material.

7. An arrangement as claimed in claim 6, wherein said metallic material comprises sheet metal.

8. An arrangement as claimed in claim 1, wherein said cannula guarding means comprises a housing structure mounted on the forward end of said at least one second slide member so as to encompass at least the tip of the cannula in the extended mutually looked position of said slide members.

9. An arrangement as claimed in claim 1, wherein means provides for visual indication of the extended locked position of said slide members.

10. An arrangement as claimed in claim 9, wherein said visual indication means comprises an opening in at least one of said slide members.

11. An arrangement as claimed in claim 10, wherein said opening is formed proximate the forward end of said first slide member.

12. A method of actuating a controlled motion lock arrangement for protecting a cannula of a catheter insertion device, said device including a housing for receiving a first end of a cannula, said cannula extending from an end of said housing coextensively with a longitudinal axis of said housing and having a sharp-tipped point at a second end adapted to introduce a catheter into a patient;

arranging axially displaceable multi-part slide means within a longitudinal recess formed in said housing so as to be extendable from the end of said housing receiving said cannula in parallel spaced relationship with said cannula, said method of actuating said slide means comprising:

(i) positioning a first slide member in slidable contact with wall surfaces of said housing recess, engaging structure on said first slide member with a locking post structure formed in said housing recess for limiting the extent of outward movement of said first slide member from said housing;

(ii) arranging at least one second slide member within said first slide member so as to be axially displaceable with respect to said first slide member having cannula tip guarding means mounted on a leading end of said at least one second slide member; locking said first slide to said locking post upon said at least one second slide member being extended; and locking said at least one second slide member to said first slide member in the outermost extended positions of said slide members while generating an audible signal indicative thereof and said guarding means protectively extends about the cannula tip.

13. A method as claimed in claim 12, wherein said locking post comprises a stepped structure, said first slide member having a lateral protuberance at the trailing end which is engaged with said locking post to limit axial movement of said first slide member from said housing.

14. A method as claimed in claim 13, wherein a resiliently deflectable tab is formed in said first slide member proximate the trailing end thereof, said at least one second slide member when fully retracted within said first slide member inhibiting deflection of said tab and, upon being extended outwardly of said first slide member, releasing said tab means such that said tab deflects into engagement with a forward surface on said locking post and in cooperation with said lateral protuberance locks said first slide member into locked engagement with said locking post.

15. A method as claimed in claim 12, wherein a cutout is provided in said at least one second slide member proximate the rearward end thereof; a resiliently deflectable tab being formed in said first slide member proximate the forward end thereof, whereby upon predetermined extension of said at least one second slide member relative to said first slide member, said resiliently deflectable tab engages into said cutout so as to lock said slide members into relative extended positions while concurrently generating an audible sound during engagement of said tab in said cutout indicative of the locking together of said slide members.

16. A method as claimed in claim 12, wherein said slide members are each of a generally box-shaped configuration in cross-section, said locking of said first slide member to said locking post and said locking of said at least one second slide member to said first slide member being effected in at least one wall surface of the respective slide member.

17. A method as claimed in claim 16, wherein said slide members are each constituted of a metallic material.

18. A method as claimed in claim 17, wherein said metallic material comprises sheet metal.

19. A method as claimed in claim 12, wherein said cannula guarding means comprises a housing structure mounted on the forward end of said at least one second slide member so as to encompass at least the tip of the cannula in the extended mutually looked position of said slide members.

20. A method as claimed in claim 12, wherein visual indication is provided for the extended locked position of said slide members.

21. A method as claimed in claim 20, wherein said visual indication comprises forming an opening in at least one of said slide members.

22. A method as claimed in claim 21, wherein said opening is formed proximate the forward end of said first slide member.

* * * * *